US012616464B2

(12) United States Patent
Awtrey et al.

(10) Patent No.: US 12,616,464 B2
(45) Date of Patent: May 5, 2026

(54) STABILIZATION DEVICES

(71) Applicant: WRIGHT MEDICAL TECHNOLOGY, INC., Memphis, TN (US)

(72) Inventors: George Matthew Awtrey, Bartlett, TN (US); Robert Michael Carlo, III, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 330 days.

(21) Appl. No.: 18/048,896

(22) Filed: Oct. 24, 2022

(65) Prior Publication Data

US 2023/0181184 A1    Jun. 15, 2023

Related U.S. Application Data

(60) Provisional application No. 63/265,198, filed on Dec. 10, 2021.

(51) Int. Cl.
*A61B 17/064* (2006.01)
*A61B 17/00* (2006.01)
(Continued)

(52) U.S. Cl.
CPC *A61B 17/0642* (2013.01); *A61B 2017/00867* (2013.01); *A61B 17/064* (2013.01);
(Continued)

(58) Field of Classification Search
CPC . A61B 17/0642; A61B 17/068; A61B 17/848;
A61B 17/064; A61B 17/0643; A61B
17/0644; A61B 17/0682; A61B 17/08;
A61B 17/083; A61B 17/10; A61B
17/076; A61B 17/0641; A61B 17/0646;
A61B 17/8004; A61B 17/809;
(Continued)

(56) References Cited

U.S. PATENT DOCUMENTS 4,741,336 A * 5/1988 Failla ................. A61B 17/0643
227/181.1
6,554,852 B1    4/2003 Oberlander
(Continued)

FOREIGN PATENT DOCUMENTS

| EP | 1764042 A2 | 3/2007 |
| WO | 2017004221 A1 | 1/2017 |
| WO | 2020139938 A1 | 7/2020 |

OTHER PUBLICATIONS

Partial European Search Report issued in connection with European Patent Application No. 22203686.5, Apr. 13, 2023, 13 pages.
(Continued)

*Primary Examiner* — Marcela I. Shirsat
(74) *Attorney, Agent, or Firm* — DUANE MORRIS LLP

(57)    ABSTRACT

Stabilization device embodiments for use in orthopedic procedures to couple to target areas of tissue. Stabilization devices described can be used to fuse, fix, provide a preselected spacing, and/or provide a preselected compression to target areas during use. Stabilization devices can be coupled to target areas using alignment elements such as pins, k-wires, and/or screws.

18 Claims, 13 Drawing Sheets

(51) Int. Cl.

| | |
|---|---|
| *A61B 17/068* | (2006.01) |
| *A61B 17/08* | (2006.01) |
| *A61B 17/10* | (2006.01) |
| *A61B 17/56* | (2006.01) |
| *A61B 17/68* | (2006.01) |
| *A61B 17/84* | (2006.01) |

(52) U.S. Cl.

CPC ....... *A61B 17/0643* (2013.01); *A61B 17/0644* (2013.01); *A61B 2017/0645* (2013.01); *A61B 2017/0646* (2013.01); *A61B 17/0682* (2013.01); *A61B 17/083* (2013.01); *A61B 17/10* (2013.01); *A61B 2017/564* (2013.01); *A61B 2017/681* (2013.01); *A61B 17/848* (2013.01)

(58) Field of Classification Search

CPC .... A61B 2017/00867; A61B 2017/564; A61B 2017/681; A61B 2017/0645; A61B 2017/0646; A61B 2017/0648

USPC ......... 606/75, 53, 246, 279, 282, 74, 76, 78, 606/86 R, 902, 907, 911

See application file for complete search history.

(56) References Cited

U.S. PATENT DOCUMENTS

| | | | |
|---|---|---|---|
| D892,331 S | | 8/2020 | Hollis et al. |
| 2010/0125275 A1* | | 5/2010 | Kinmon ............. A61B 17/1739 |
| | | | 606/103 |
| 2011/0118796 A1 | | 5/2011 | Reiley et al. |
| 2013/0123863 A1 | | 5/2013 | Hollis et al. |
| 2013/0144343 A1 | | 6/2013 | Arnett et al. |
| 2013/0267956 A1 | | 10/2013 | Terrill et al. |
| 2015/0313592 A1 | | 11/2015 | Coillard-Lavirotte et al. |
| 2016/0192930 A1 | | 7/2016 | Finley et al. |
| 2017/0065276 A1* | | 3/2017 | Weiner ............... A61B 17/0642 |
| 2017/0202552 A1* | | 7/2017 | Coleman ........... A61B 17/0642 |
| 2018/0008263 A1* | | 1/2018 | Goldstein .......... A61B 17/8095 |
| 2018/0353172 A1 | | 12/2018 | Hartdegen et al. |

OTHER PUBLICATIONS

Extended European Search Report issued in connection with corresponding European Patent Application No. 22203686.5, Jul. 14, 2023, 14 pages.

* cited by examiner

STABILIZATION DEVICES

CROSS-REFERENCE TO RELATED APPLICATION

This application claims priority under 35 U.S.C. § 119(e) to U.S. Provisional Application No. 63/265,198, filed on Dec. 10, 2021, the entire contents of which are incorporated herein by reference.

TECHNICAL FIELD

The present disclosure relates to the field of implants for use in medical procedures. In particular, stabilization devices described herein can be used to join target areas of tissue.

BACKGROUND

Devices and methods of stabilization of tissue for use in orthopedic procedures may include plates, staples, and devices having a solid body.

Current staples consist of two or multi-leg devices with in-line compression and are meant to be used without discrimination across joint/bone surfaces.

FIGS. 1-3 depict prior art staples. As shown in FIG. 1, staple 2 includes multiple legs 4. Bridging member 6 is formed such that distal ends 8 of legs 4 are closer together than ends 10 connected to bridging member 6.

FIG. 2 depicts staple 12 positioned in tissue 14. Staples having bridges may cause soft tissue damage and/or irritation. As shown in FIG. 2, bridge 16 protrudes beyond tissue 14. Thus, site 18 indicates a potential location of irritation in the surrounding soft tissue. When in use, distal ends 20 of legs 22 of staple 12 are positioned further apart than ends 24 connected to bridging member 16. As shown in FIG. 2, positioning of the distal ends may affect the ability of the staples to couple target areas of tissue such that the distance between the target areas is equidistant. In some instances, this variable distance between the legs may cause uneven compression across the site of the tissue repair which may lead to delayed and/or malunion of the target areas of the tissue being repaired. The target areas of the tissue may include bone, bone segments and/or adjacent areas of bone.

Further, as shown in FIG. 3, legs 26, 26' have reduced torsional stability due to the geometry of staple 28 shown in FIGS. 2-3. In particular, staple 28 has a triangular shaped profile.

Thus, there is a continuing need for an improved external fixator that can provide such adaptability.

Implants for use in surgery need to be constructed in a manner that reduces or inhibits potential for irritation during use. Designs that provide surgeons with superior control, accuracy and performance are of particular interest. This results in reduced damage, heat and trauma to the tissues and leads to faster operations, more first-time results and an overall improvement in post-surgery healing.

SUMMARY

A stabilization device can include a first leg, a second leg substantially parallel to the first leg, and one or more cross-members coupling the first leg to the second leg. The one or more cross-members couple to the first and second legs at a predetermined distance from at least one end of each of the first and second legs. Each of the first and second legs includes an opening along longitudinal axes of the first and second legs. The first leg of stabilization device can be positioned substantially within a target area of tissue during use.

In some instances, the first and second legs of the stabilization device are positioned completely within at least two target areas of tissue such that the stabilization device couples the at least two target areas of tissue during use.

During use the one of more cross-members can extend from a first target area of tissue to a second target area of tissue at an interface of the first and second target areas. Further, during use the first leg can be positioned within the first target area and the second leg can be positioned within the second target area.

The stabilization device can be secured to target tissue using one or more alignment elements during use. For example, the stabilization device can be secured to target tissue using one or more pins during use.

In some instances, the first and second legs and the one or more cross-member of the stabilization device can be formed from a metal alloys. For example, the first and second legs and the one or more cross-members can be formed from Nitinol.

An embodiment of a stabilization device can include a first leg and a second leg substantially parallel to the first leg. The stabilization device can also include one or more cross-members coupling the first leg to the second leg. The ends of each of the first and second legs can extend beyond an outermost edge of the cross-member such that a plane that includes a first end of the first leg and a first end of the second leg does not contact any of the one or more cross-members. In particular, the legs may extend beyond cross-member along a longitudinal axis of the legs. The stabilization device can include first and second legs and the one or more cross-members are formed from a metal alloy such as Nitinol. Each of the first and second legs of the stabilization device can include an opening along longitudinal axes of the first and second legs. The stabilization device can be secured to target areas of tissue using alignment elements such as pins during use.

The stabilization device can be positioned within at least two target areas of tissue such that the stabilization device couples the at least two target areas of tissue and the one or more cross-members extend from the first target areas of tissue to the second target area of tissue at an interface of the at least two target areas during use.

A stabilization device system can include a first alignment element, a second alignment element, a cut guide, an inserter device, and a stabilization device having a first leg, a second leg, and a cross-member coupling the first leg to the second leg. The stabilization device can include at least one end of each of the first and second legs extending beyond an outermost edge of the cross-member along a longitudinal axis of the stabilization device.

In such an embodiment, the stabilization device can be secured to target areas of tissue using the first and second alignment elements, such as pins during use.

An embodiment of an orthopedic stabilization device can include a first leg having a first opening, a second leg having a second opening, and a cross-member coupling the first leg to the second leg. During use alignment elements can be used for positioning the orthopedic stabilization device in target tissue. Alignment elements can be capable of coupling to openings of legs of the orthopedic stabilization device during use. The orthopedic stabilization device secures a target area of tissue during use.

An embodiment of an orthopedic implant system can include at least two stabilization devices that include a first leg having a first opening, a second leg having a second opening, and a cross-member coupling the first leg to the second leg and alignment elements for coupling to openings of legs during use. At least two stabilization devices secure a target area of tissue during use.

In some instances, an orthopedic implant system can include at least two stabilization devices that can be positioned such that ends of first legs of each of the at least two stabilization devices are proximate to each other during use.

Further, an embodiment of an orthopedic implant system can include at least two stabilization devices that can be positioned such that cross-members are positioned proximate to each other during use.

During use an orthopedic implant system can include at least two stabilization devices positioned such that cross-members are positioned proximate to each other and ends of first and second legs are positioned such that the first openings of the first legs are proximate to each other and the second openings of the second legs are proximate to each other.

A stabilization device can include multiple legs. For example, a stabilization device can include two legs that are substantially parallel. The legs can be positioned at opposite ends of one or more cross-members that couple the legs to each other. Ends of the legs can extend beyond an outermost edge of the cross-member.

The stabilization devices of the present disclosure and elements thereof can be formed from a metal or an alloy. For example, the legs and the cross-members can be formed from a metal alloy. The legs and the cross-members of the stabilization devices can be formed from a nickel titanium alloy such as Nitinol.

The legs of the stabilization devices can include openings. The openings in the legs can be formed along longitudinal axes of the legs. The openings can be used to position and/or secure the stabilization device to the target tissues using alignment elements such as pins, k-wires, and/or screws. For example, pins can be positioned in the target tissues and then the stabilization device can be positioned based on the locations of the pins. The stabilization device can be secured to the target tissue using pins during use.

A stabilization device system can include alignments elements, such as pins, a cut guide, drill guides, and a stabilization device that includes legs and at least one cross-member. Pins can be used to position and/or secure stabilization devices to a target tissue. For example, some embodiments of stabilization device systems can include at least two pins for each stabilization device.

The one or more cross-members can couple the legs to each other. In some embodiments, ends of the legs extend beyond an outermost edge of the cross-members.

An orthopedic implant can include legs that are constructed such that they engage with alignment elements. Alignment elements such as pins, screws, k-wires, or the like can be used to position a stabilization device. In some embodiments, the stabilization devices can be secured to the target tissue using one or more alignment elements during use.

Some embodiments of stabilization devices can include alignment elements capable of both positioning and securing a stabilization device. Such alignment elements can include but are not limited to pins, screws, k-wires, or like.

The stabilization devices can include structures and/or elements that engage alignment elements such that the stabilization devices can be positioned and/or secured to a target tissue. For example, each of the legs can include an opening that extends along the longitudinal axis of the leg.

Such openings can have a predetermined geometry that conforms to a selected alignment element such as a pin, screw, k-wire, or the like. In an embodiment, both legs have openings extending from a first end to second end of the leg such that alignment elements positioned in the openings extend a predetermined distance in the openings. For example, pins can extend a full length of the openings. During use, alignment elements ensure that the stabilization devices maintain a predetermined position relative to the target area of the tissue being repaired. In this manner, an orthopedic implant such as a stabilization device, can be secured to the target area of the tissue during use.

The cross-members couple the legs to each other. The cross-members can couple the legs at predetermined positions along the length of the legs. The cross-members can have varying geometries. For example, a cross-member can have an arcuate structure such as an arc or S-shaped structure, a truss structure, a triangular structure, an inverted triangular structure, etc. Some embodiments can include multiple cross-members connecting legs.

An orthopedic implant system can include two or more stabilization devices. Each of the stabilization devices can include legs having openings and a cross-member connecting the legs. The legs can be secured to a target area of a tissue using alignment elements coupled to the openings during use. In some embodiments, the at least two stabilization devices secure a target area of the tissue during use. Stabilization devices can be positioned such that ends of first legs are positioned proximate to each other during use. In alternate embodiments, stabilization devices can be positioned such that cross-members are positioned proximate to each other during use.

In some implant embodiments, multiple stabilization devices can be positioned such that the cross-members are positioned proximate to each other and ends of the legs are positioned such that the openings of a first legs are proximate to each other and the second openings of the second legs are proximate to each other during use.

A method of implanting a stabilization device can include drilling a first pilot hole, positioning a first alignment pin in the first pilot hole, drilling a second pilot hole using a drill guide, positioning a second alignment pin in the second pilot hole, positioning a cut guide over the first and second alignment pins, making a cut for a cross-member of the stabilization device and inserting stabilization device.

Methods for implanting a stabilization device can include drilling pilot holes. In some embodiments, pilot holes can be drilled using a drill guide. Pilot holes can be drilled at selected locations in target tissues. The locations for the pilot holes can be selected based on the type of procedure, type of injury, anatomy of the patient, etc. The method also includes positioning an alignment element in one of the pilot hole. For example, an alignment pin can be positioned in each of the pilot holes. After positioning of the alignment elements, a cut guide can be positioned over the alignment elements. The cut guide can be used to make a cut for a cross-member of the stabilization device. The stabilization device can then be implanted. In some instances, portions of the stabilization device can engage with the alignment elements.

Although the invention has been described in terms of exemplary embodiments, it is not limited thereto. Rather, the appended claims should be construed broadly, to include other variants and embodiments of the invention, which can be made by those skilled in the art without departing from the scope and range of equivalents of the invention.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts.

DETAILED DESCRIPTION

Figure 1:
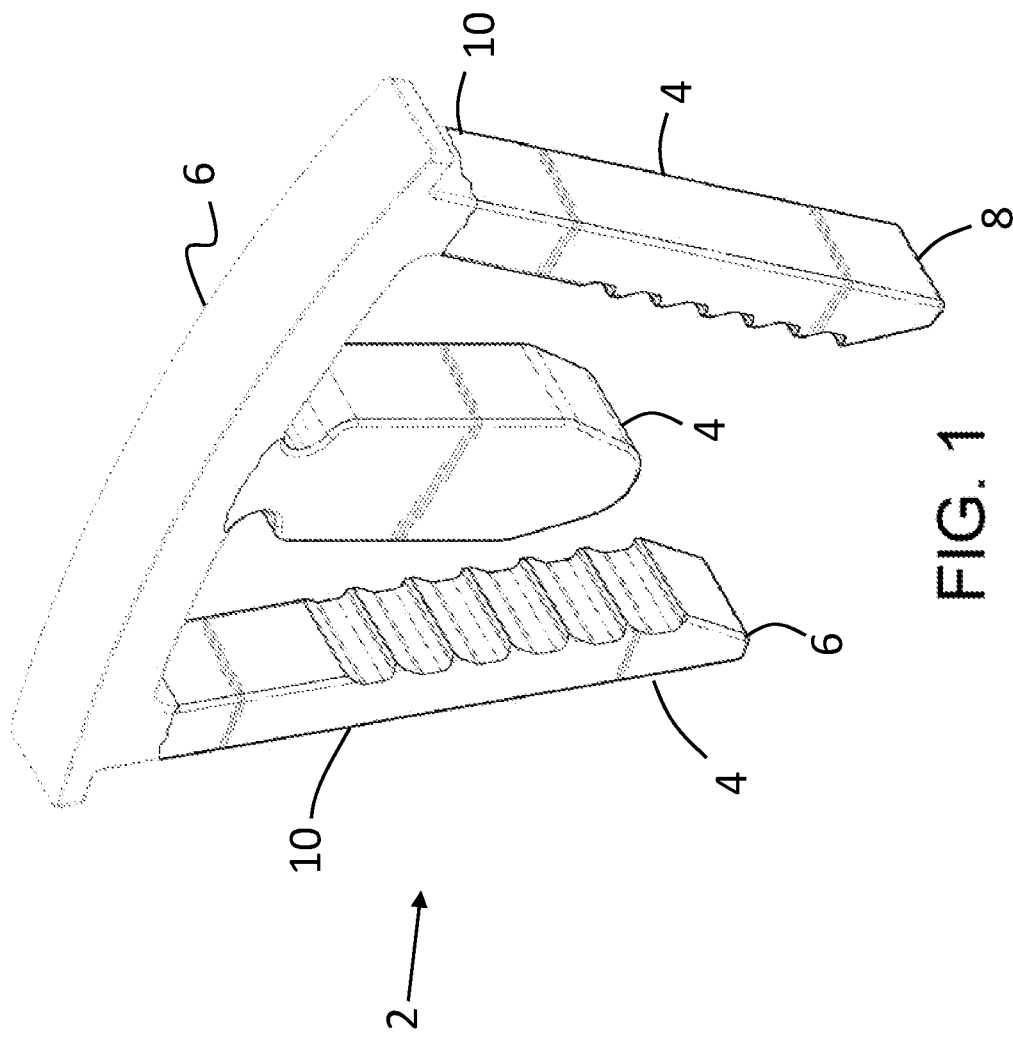
FIG. 1 is an illustration of a prior art example of a staple.
Figure 2:
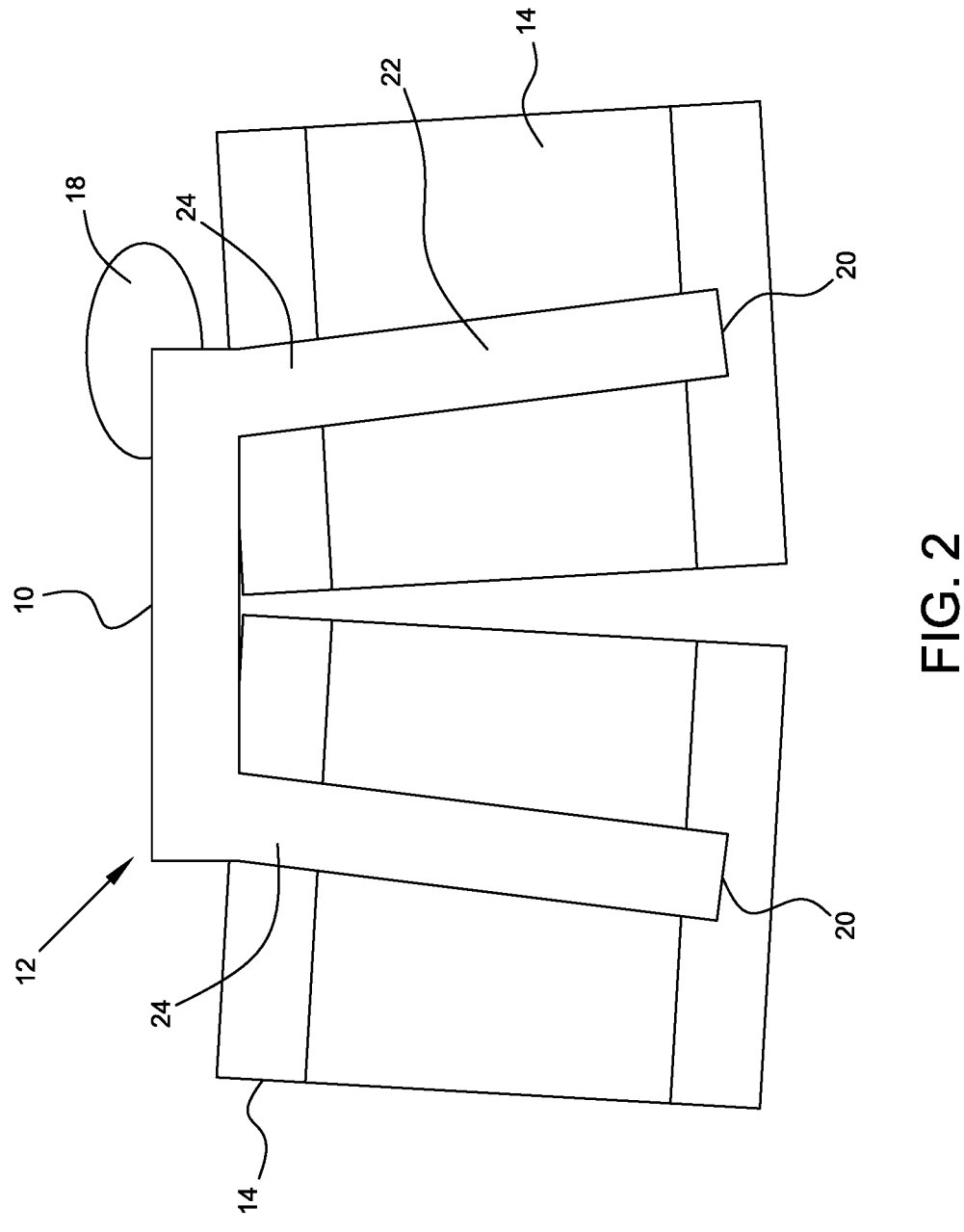
FIG. 2 is an illustration of a prior art example of a staple.
Figure 3:
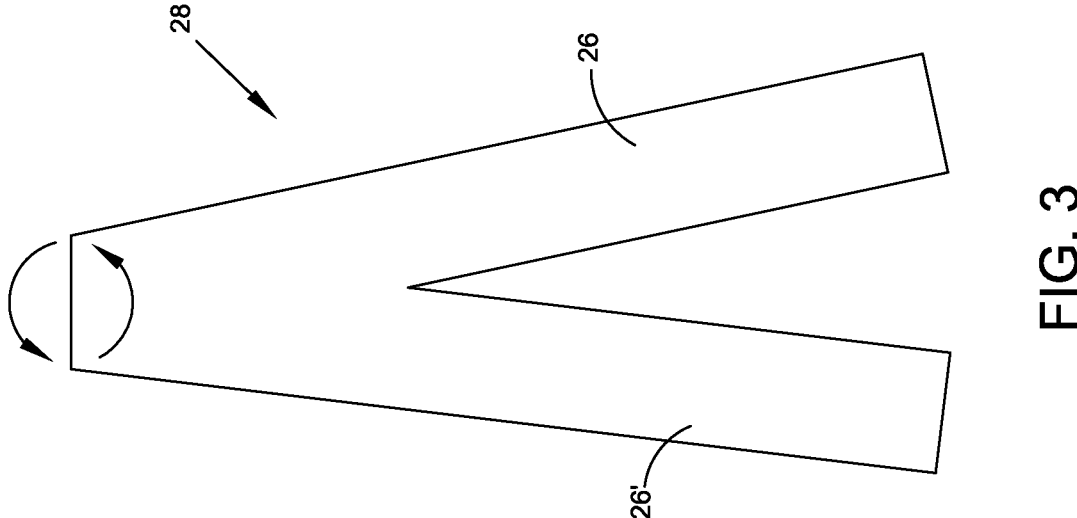
FIG. 3 is an illustration of a prior art example of a staple.

This description of the exemplary embodiments is intended to be read in connection with the accompanying drawings, which are to be considered part of the entire written description. The drawing figures are not necessarily to scale, and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including matters of logic with respect to arrangement of steps, operational flow, order of components, or orientation of components, plain meaning derived from grammatical organization or punctuation, and the number or type of embodiments described in the specification.

The stabilization devices described herein can be used to fix and/or fuse target areas of a tissue. For example, the stabilization devices can be used to fix and/or fuse to separate areas of a bone.

The stabilization devices and elements thereof can be formed from a material usable in the prosthetic arts, including, but not limited to metals such as titanium and/or tantalum, alloys such as titanium alloys, nickel titanium alloys (i.e., Nitinol), chrome cobalt, surgical steel, or any other total joint replacement metal and/or ceramic, sintered glass, artificial bone, or a combination thereof. In some alternate embodiments, portions of a stabilization device can be formed from a suitable durable biologic material or a combination of metal and biologic material, such as a biocompatible bone-filling material.

Stabilization devices as described herein can be formed utilizing one or more methods including, but not limited to machining such as electrical discharge machining, for example, wire electrical discharge machining (WEDM), molding, additive manufacturing such as 3D printing or laser sintering, and/or extrusion.

For example, the legs and the cross-members of an embodiment can be formed from a metal alloy. In some embodiments, shape memory materials such as nickel titanium alloys can be used for orthopedic implants such as stabilization devices. For example, the legs and the cross-members of the stabilization devices in some embodiments can be formed from a nickel titanium alloy such as Nitinol. Nitinol has historically had various uses in medicine, for example, in cardiac stents, orthodontic wires, and musculoskeletal implants due to Nitinol's shape memory properties Referring to FIG. 4, an orthopedic implant according to some embodiments is a stabilization device 30. Stabilization device 30 can be used to join and compress two tissue parts A and B across an interface C to promote healing and formation of a permanent joint at the interface C between the two tissue parts A and B. In the example shown, the two tissue parts A and B are two ends of a long bone facing across the interface C. The interface C can be the result of a fracture of the long bone or as a result of an osteotomy.

As such, stabilization devices 30 can be useful in joint fusions including osteotomy procedures. For example, stabilization devices can be used in osteotomy procedures such as Evans's osteotomy, Cotton osteotomy, and tibial osteotomy to assist in healing of the two bone parts involved in the osteotomy. In the illustrated example in FIG. 4, each of the bone pieces A and B comprises cancellous bone portions 32, 34 and their respective cortical bone portions 33, 35.

In some embodiments, stabilization devices can provide the selected spacing between target areas of tissue. For example, stabilization device 30 is secured between two target areas of tissue.

Stabilization devices 30 can be formed utilizing one or more methods including, but not limited to machining such as electrical discharge machining, for example, wire electrical discharge machining (WEDM), molding, additive manufacturing such as 3D printing or laser sintering, and/or extrusion.

Figure 4:
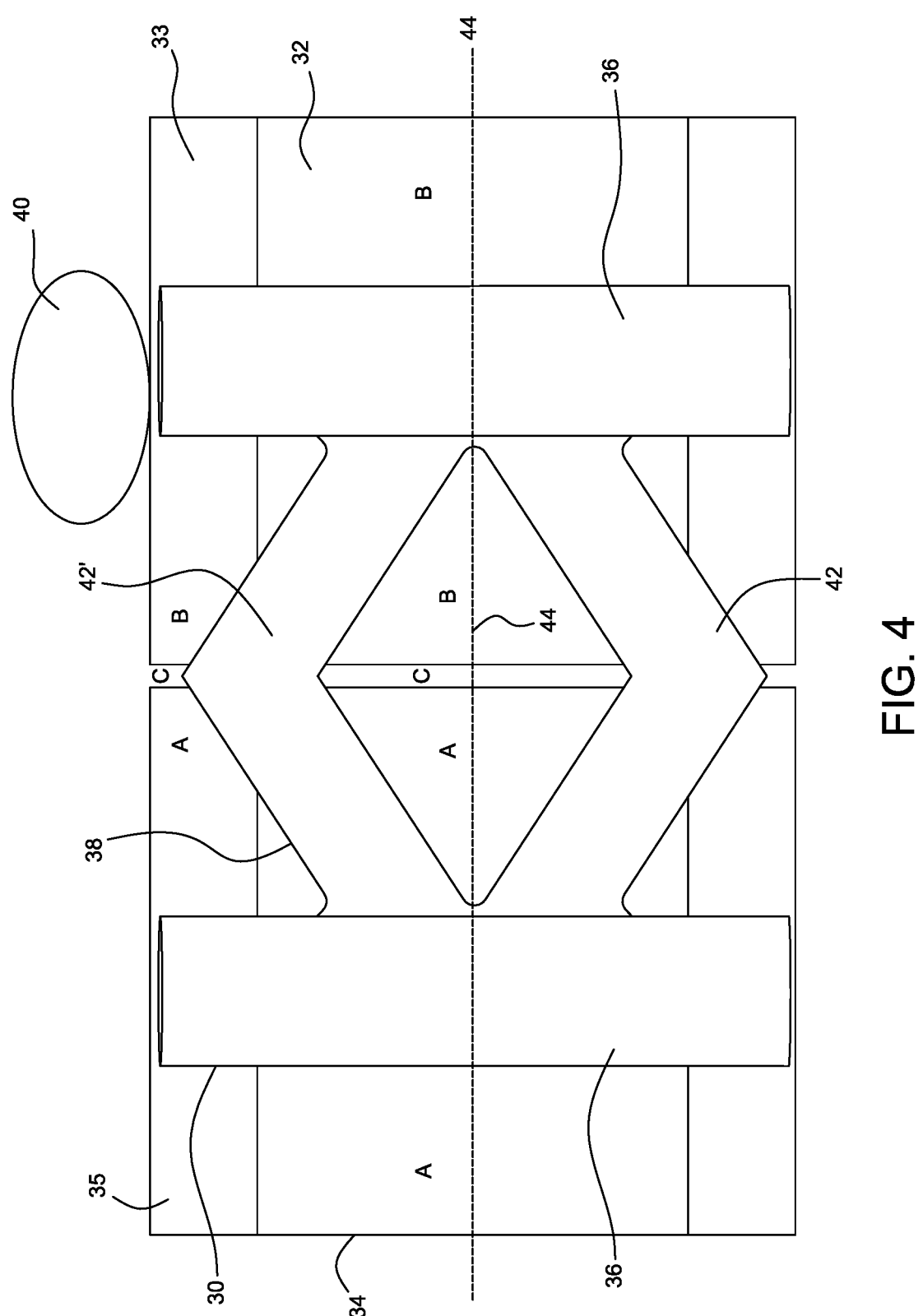
FIG. 4 is a cross-sectional view of an embodiment of a stabilization device positioned in tissue.

FIG. 4 depicts stabilization device 30 positioned in target areas of tissue 32, 33, 34, 35. Stabilization device 30 includes two legs 36 and spacer structure 38 that includes cross-members 42, 42'. As shown, stabilization device 30 is implanted in target areas of tissue 32, 33, 34,35.

Positioning of stabilization device can be used to control the position of target areas relative to each other. For example, a position for a stabilization device can be selected to provide a predetermined positioning of target areas 32, 33 relative to target area 34, 35.

During use a stabilization device can be positioned within at least two target areas of tissue such that the stabilization device couples the at least two target areas of tissue at an interface. For example, as shown in FIG. 4, the stabilization device 30 is implanted in tissue parts A, B such that a portion of the stabilization device 30 crosses the interface C between the tissue parts A, B. Thus, during use a stabilization device 30 can promote healing and formation of a permanent joint at the interface C between the two tissue parts A and B. As shown in FIG. 4, the stabilization device 30 is positioned within target areas, for example tissue parts A, B, and only extends beyond an outer surface of individual target areas at the interface C of the tissue parts A, B. In particular, As shown in FIG. 4, the two legs 36 of the stabilization device 30 do not extend along the longitudinal axis of the legs of the stabilization device beyond target areas of tissue 32, 33, 34, 35.

By limiting the positioning of the stabilization devices within the target areas of tissue irritation of surrounding tissues may be reduced, if not eliminated. For example, in the embodiment depicted in FIG. 4 the legs 36 of the stabilization device 30 should not protrude beyond the surface of the tissue to reduce irritation of the surrounding tissues. In particular, during use the stabilization device embodiment shown in FIG. 4 can be positioned in a target area of bone such that the legs 36 of the stabilization device 30 do not protrude beyond the surface of the bone to reduce irritation of the surrounding tissues.

In some embodiments, elements of stabilization devices such as legs, spacer elements, and/or cross-members should not protrude beyond surfaces of target areas except at an interface between the target areas.

As shown in FIG. 4, legs 36 do not extend into surrounding tissues 40.

Spacer structures may have varying geometries. Spacer structures may include cross-members of varying shapes. Some embodiments can include multiple cross-members connecting legs. For example, a cross-member can be an arcuate structure such as an arc, an S-structure, a truss structure, a triangular structure, an inverted triangular structure, etc. Cross-members can couple the legs to each other.

As shown in FIG. 4, spacer structure 38 includes cross-members 42, 42'. Cross-members can couple to the legs at predetermined positions along the length of the legs. Locations of the coupling can be selected based on tissue type, location and/or type of injury, anatomy of patient, desired distance between the target tissue areas, desired compression, and/or needs of the surgical team. For example, in the embodiment shown in FIG. 4 the cross-members 42, 42' are positioned symmetrically relative to a horizontal centerline 44 of the stabilization device 30.

A stabilization device utilizing legs and cross-members can be selected to provide a predetermined strength, compression, distance between target areas. In some embodiments, it may be desired to provide a stabilization device which provides one or more of the predetermined characteristics while reducing a footprint of the stabilization device in the body of the patient.

Figure 5:
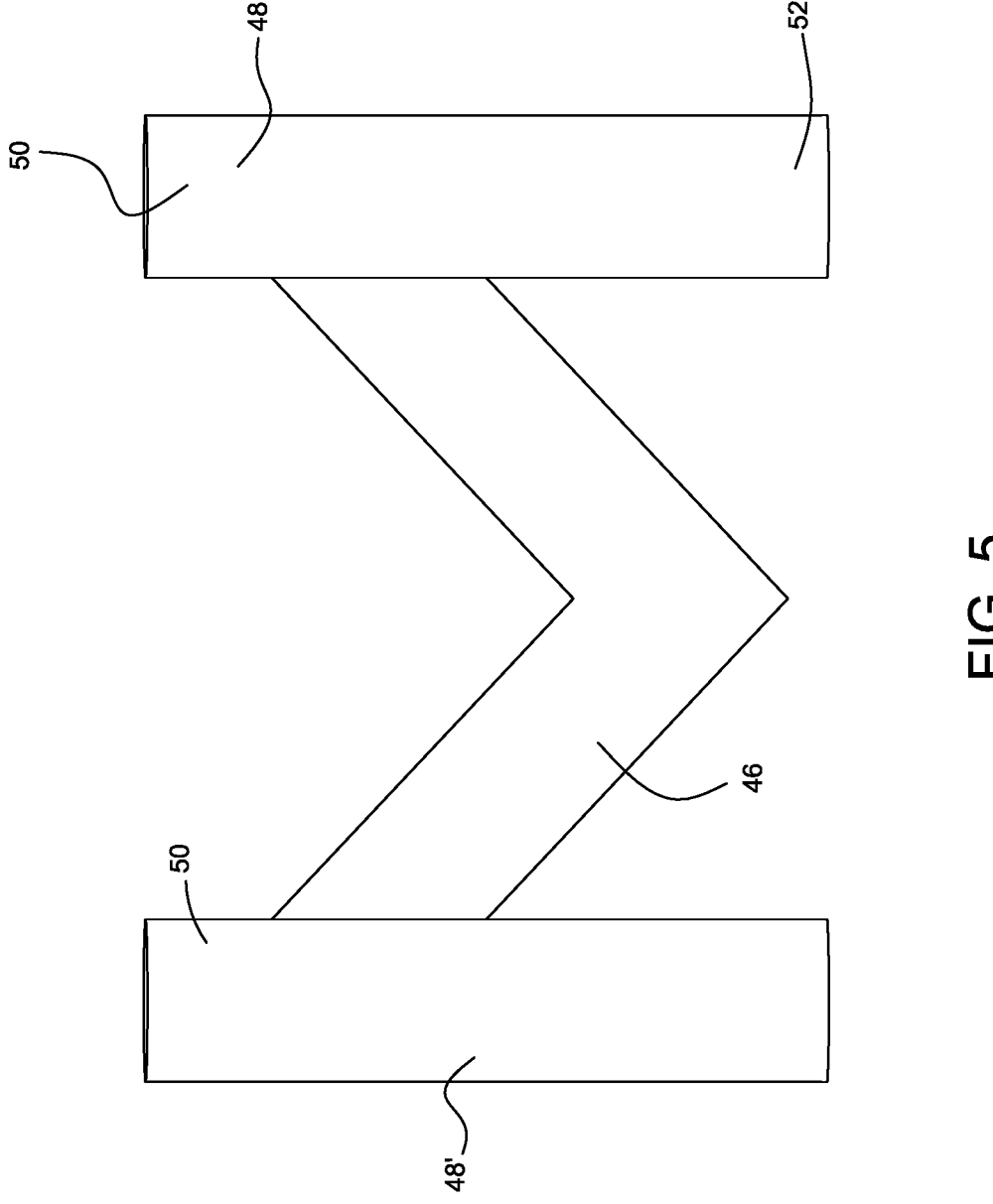
FIG. 5 is a front view of an embodiment of a stabilization device.

In some embodiments, as shown in FIG. 5, a cross-member 46 is coupled to the legs 48, 48' near a proximate end 50 of the legs 48, 48'. The cross-member 46 is positioned such that the proximate ends 50 of the legs 48, 48' do extend beyond a plane of the outermost portions of cross-members. However, when the embodiment of stabilization device shown in FIG. 5 is positioned in a target area of tissue the legs can be positioned such that the legs do not extend beyond the target area of tissue. For example, the stabilization device can be positioned such that neither the legs or cross-members enter the surrounding tissue. In other words, the stabilization device can be positioned substantially within target areas of tissue.

The stabilization device embodiment shown in FIG. 5 includes legs 48, 48' that are substantially parallel to each other. In some embodiments, stabilization devices can be formed such that legs have a predetermined angle of entry into a target area such as a bone. For example, in some embodiments one end of legs of a stabilization device can diverge while the opposite ends of the legs converge.

Cross-members 42, 42', 45 of FIGS. 4-5 have planar surfaces. The planar surfaces of the cross-members can aid in positioning of the stabilization devices during use. As shown cross-members can have a width that differs from the height of the planar surface.

Figure 6:
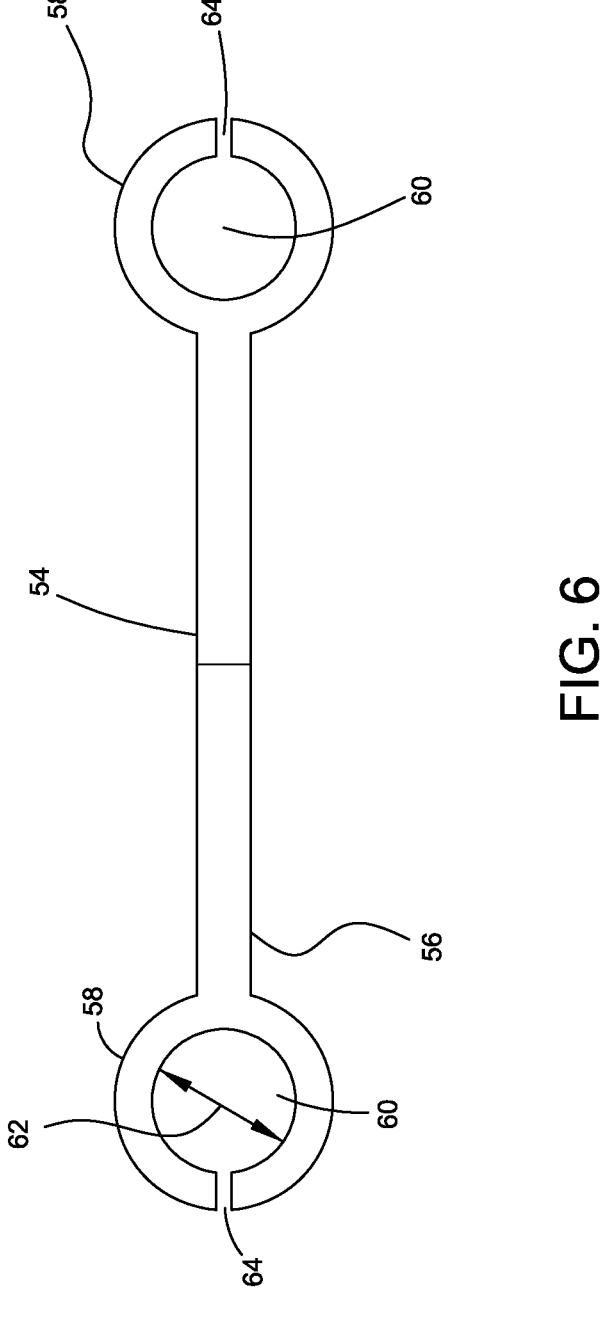
FIG. 6 is a top view of an embodiment of a stabilization device depicted in FIG. 5 and showing openings in the legs.

FIG. 6 depicts a top view of a stabilization device 54 having a cross-member 56 and legs 58. The legs 58 of the stabilization device 54 include the openings 60. Openings in the legs can be formed along longitudinal axes of the legs. Openings can be used to position and/or secure the stabilization device to target areas of tissue using alignment elements such as pins, k-wires, and/or screws. Alignment elements can be constructed to engage an opening and/or a slot of a leg of the stabilization device. For example, a diameter of an alignment element can be substantially equal to or less than the diameter 64 of the opening 60 in the leg 64 shown in FIG. 6.

As shown in FIG. 6, both legs 58 have openings 60 and slots 64 extending from a first end (not shown) to second end (not shown) of the legs. During use the alignment elements (not shown) can be positioned in the openings such that they extend a predetermined distance in the openings. For example, in some instances pins can extend a full length of the openings. Alternatively, the alignment elements may extend only partially along a length of the openings. Alignment elements may be positioned such that an end of the alignment element extends from a position in the target tissue through a portion of the opening. Alignment elements, such as pins, may be fully encompassed in the openings. For example, when a stabilization device is positioned such that the openings are positioned over an entire length of the pins.

In some embodiments, alignment elements can be removed after positioning of the stabilization device. For example, a portion of an alignment element can be removed after the stabilization device is positioned.

During use the alignment elements can ensure that implants, such as stabilization devices, maintain a predetermined position relative to one or more target areas of tissue. In this manner, an orthopedic implant such as a stabilization device can be secured to one or more target areas of tissue during use.

In some embodiments, alignment elements, such as pins, can be positioned in target areas of tissues and then the stabilization device can be positioned based on locations of the pins. Stabilization devices can be secured to target areas of tissues using alignment elements during use.

Figure 7:
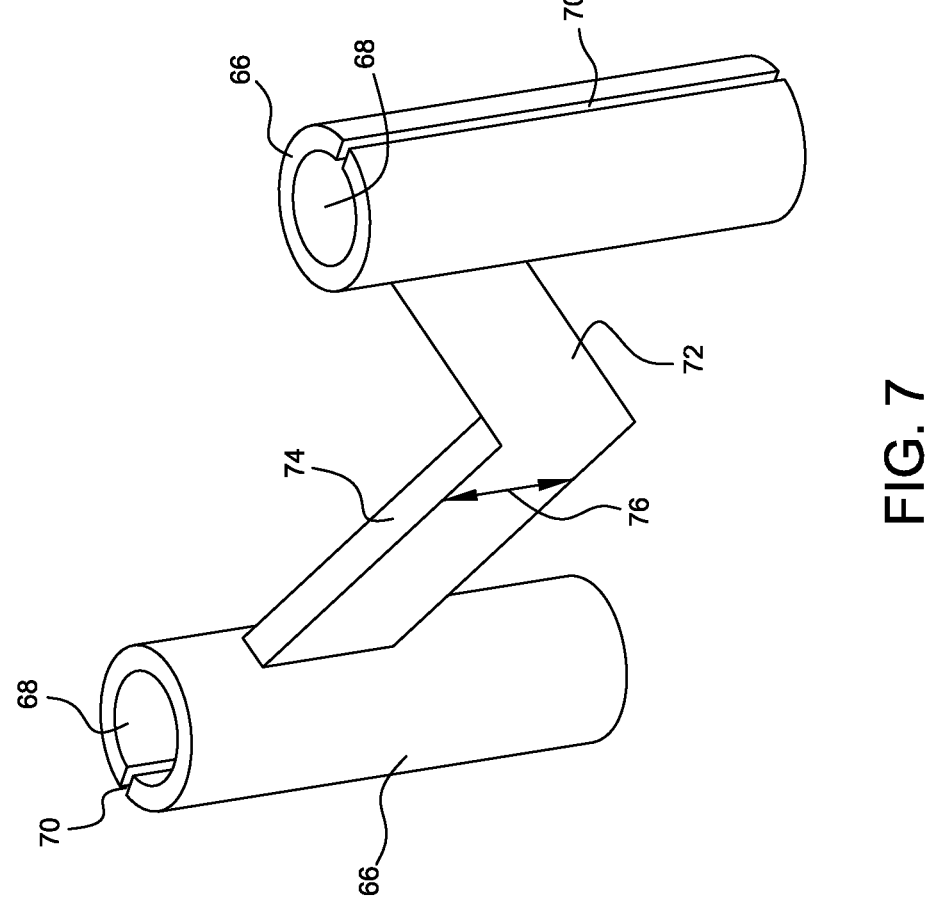
FIG. 7 is a side perspective view of an embodiment of a stabilization device depicted in FIG. 5.

FIG. 7 depicts legs 66 having both openings 68 and slot 70. As shown, the slot 70 extends the full length of the leg 66. During use the legs can engage alignment elements. Alignment elements, such as pins, screws, k-wires, or the like may be used to position a stabilization device. In some embodiments, stabilization devices can be secured to target tissue using alignment elements during use. As shown in FIG. 7, some embodiments of cross-members 72 have a thickness 74 that is substantially smaller than a length 76. Proportions of the stabilization devices and elements thereof may be selected based on desired properties for the stabilization devices. For example, cross-member dimensions can be selected based on target areas of tissue to be fused, fixed, and/or stabilized, determinations of the surgical team, type of injury, desired compression or extension between the target areas of tissue, desired strength of the stabilization device, etc.

In some embodiments, openings can include threads. Threads can be constructed to accommodate the threaded heads of screws or other threaded elements. For example, the threaded screw holes can be configured to accommodate uni-axial locking screws or poly-axial locking screws. In some embodiments the screws can be locking screws, non-locking screws, or compression screws.

Figure 8:
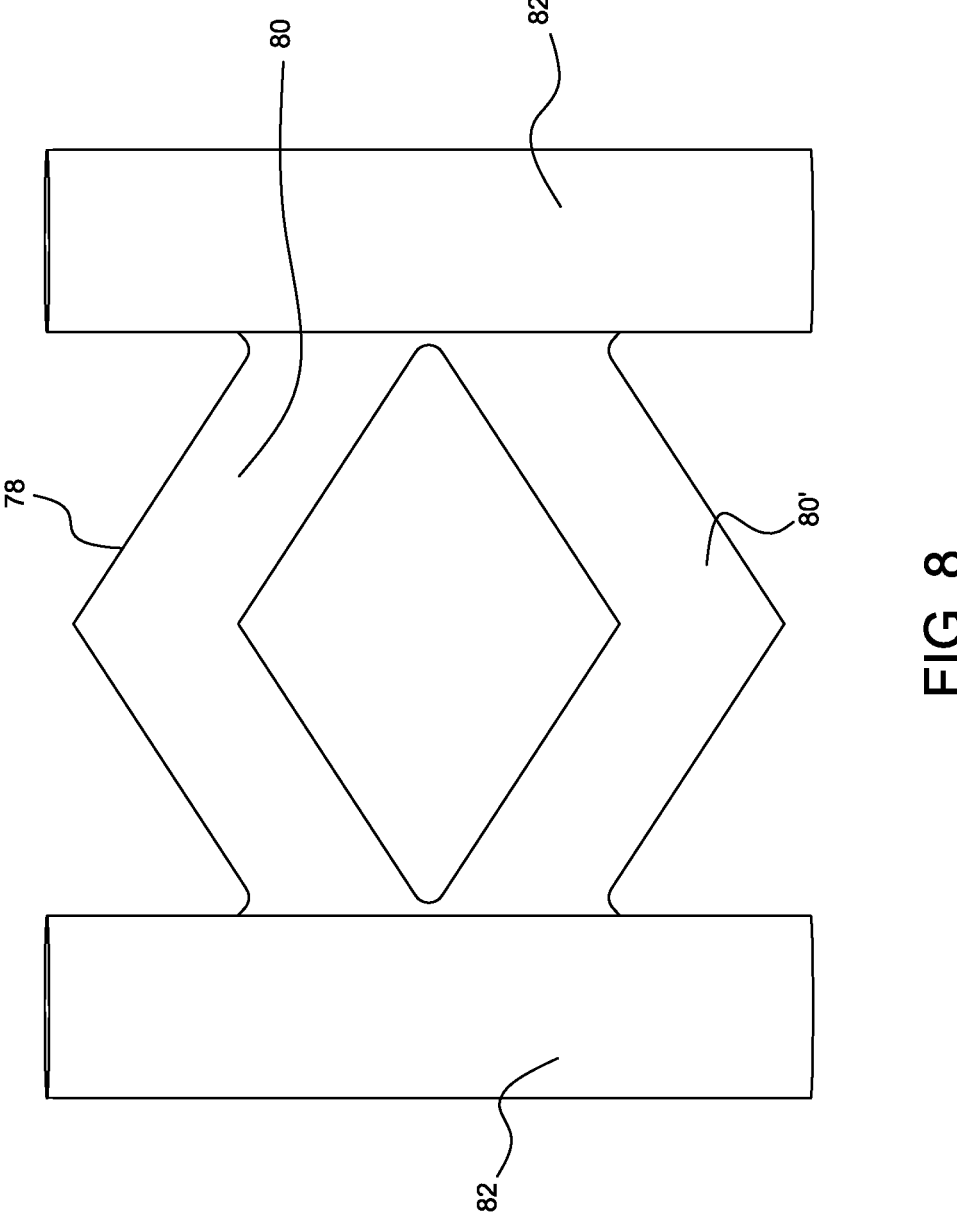
FIG. 8 is a front view of an embodiment of a stabilization device having two cross-members coupled to each of the legs of the stabilization device.
Figure 9:
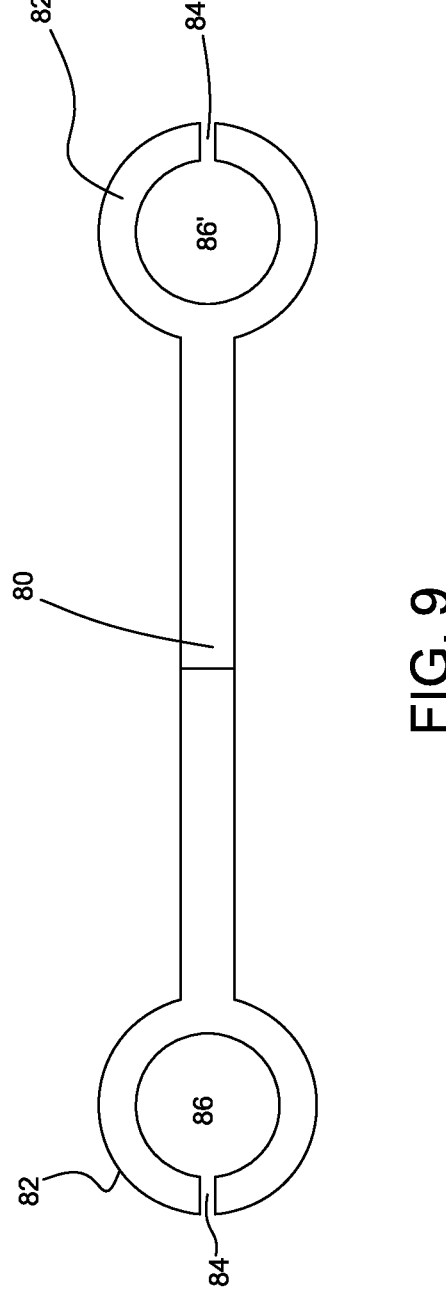
FIG. 9 is a top view of an embodiment of a stabilization device depicted in FIG. 8 and showing openings in the legs.
Figure 10:
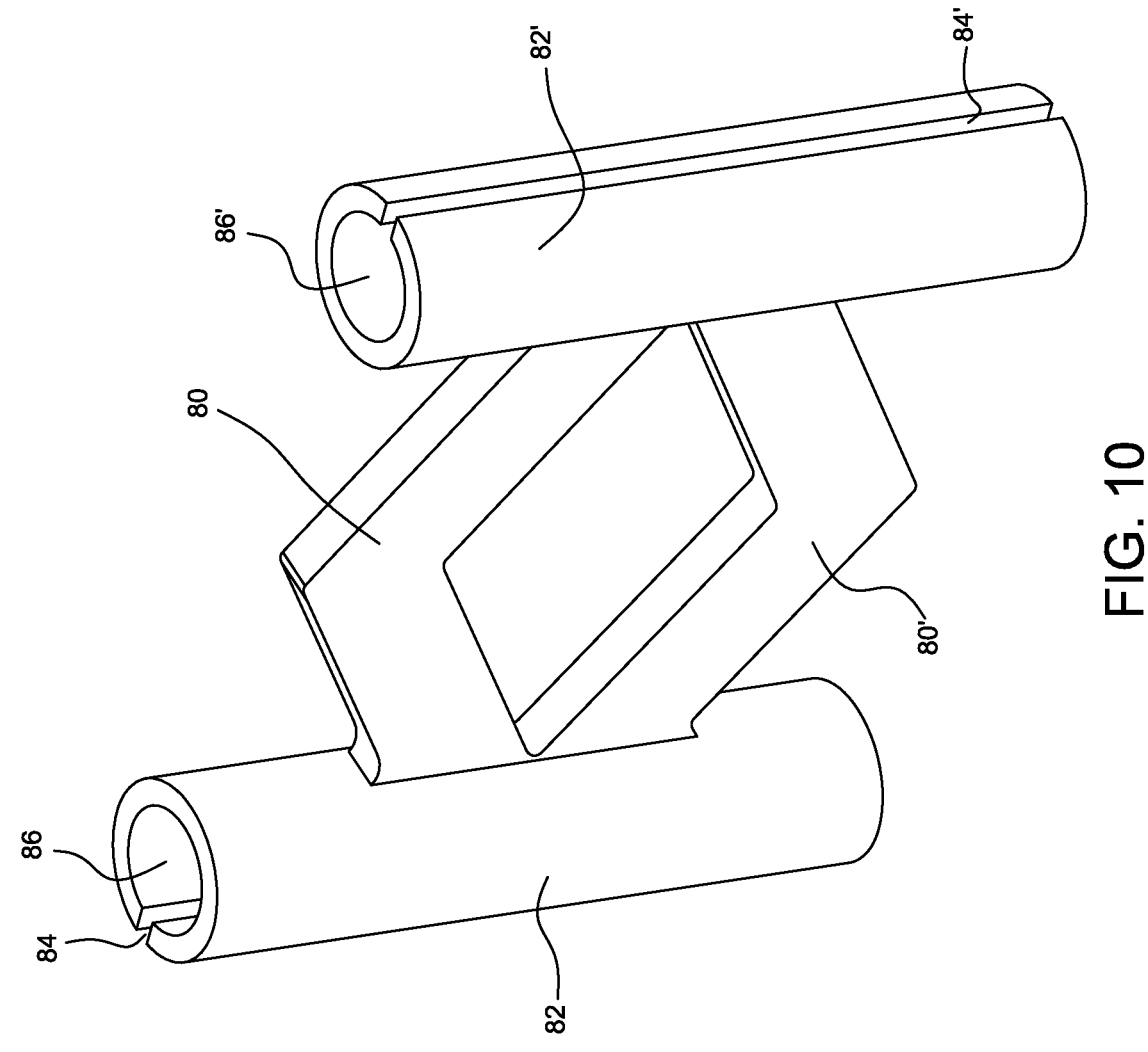
FIG. 10 is a side perspective view of an embodiment of a stabilization device depicted in FIG. 8.

FIGS. 8-10 depict an embodiment of the stabilization device 78 having two cross-members 80, 80'. Cross-members 80, 80' connect to each other and the legs 82, 82'. In alternate embodiments, the cross-members can each separately connect to the legs. In some embodiments, a number of cross-members in a stabilization device can vary. Numbers and/or configurations of the cross-members may be determined by requirements of use.

As shown in FIGS. 9-10, the slots 84, 84' and the openings 86, 86' extend the full length of the legs 82, 82'

In some embodiments, the legs can engage in a friction fit with the alignment elements or portions thereof. In alternate embodiments, the legs and/or the alignment elements can include engagement elements to couple the legs and the alignment elements together. For example, alignment elements can include a protrusion that engages with the slots in the legs.

To position a stabilization device multiple pilot holes can be drilled into the target areas of tissue to receive the alignment elements and/or the legs of a stabilization device. During use, the holes can be drilled into one or more predetermined locations of bone such that the alignment elements and/or legs of the stabilization device can be positioned in the bone.

Locations for the pilot holes can be selected based on type of procedure, type of injury, anatomy of the patient, target area limitations, type of tissue, compression desired, distance between the target areas, etc. After the pilot holes are complete the alignment elements can be positioned in the holes. For example, the alignment pins can be positioned in the pilot holes. After positioning of the alignment elements in target areas a cut guide can be positioned over the alignment elements. The cut guide can be used to make a cut for a stabilization device. For example, the cut guide can be used to make a cut for cross-members of the stabilization device. A stabilization device can then be implanted. In some instances, portions of the stabilization device can engage with the alignment elements.

An implant system can include alignment elements such as pins, a cut guide, a stabilization device that includes legs and at least one cross-member. Pins can be used to position and/or secure stabilization devices to target tissue. For example, some embodiments of implants systems can include at least two pins for each stabilization device. The cross-member can couple the legs to each other. In some embodiments, ends of the legs extend beyond an outermost edge of cross-members.

Devices can include structures and/or elements that engage alignment elements such that the devices can be positioned and/or secured to a target tissue. For example, the legs can include openings along the longitudinal axis of the leg. Such openings can have a predetermined geometry that conforms to a selected alignment element such as a pin, screw, k-wire, or the like.

Multiple devices can be employed to provide stabilization to target areas. While the use of multiple devices will now be described illustrating the use of multiple devices of the same size and configuration, it is contemplated that devices can also be of different sizes and/or configurations.

Multiple stabilization devices can be positioned to provide stabilization over a larger target area. For example, a series of devices can be coupled together using alignment elements passing through openings in legs of each individual stabilization device.

Figure 11:
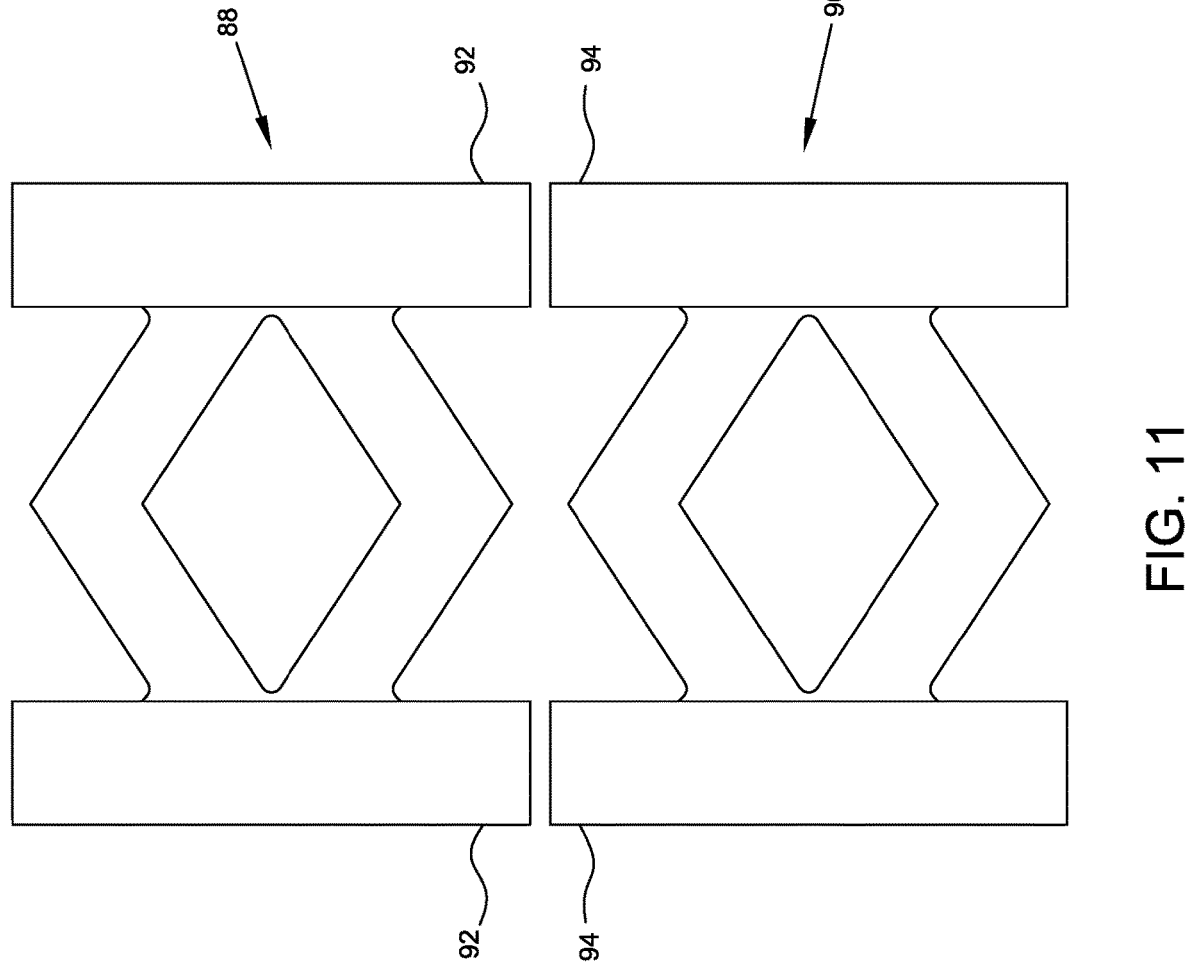
FIG. 11 depicts two stabilization devices positioned in manner to be used together to secure a target area of tissue.

An embodiment of an orthopedic implant system can include two or more stabilization devices. FIG. 11 depicts two stabilization devices 88, 90 positioned in a configuration suitable for use in an orthopedic procedure. Distal ends 92 of legs of stabilization device 88 are positioned proximate to proximal ends 94 of legs of stabilization device 90. During use alignment elements can be positioned in openings in legs and extend through openings of both legs.

Thus, in some embodiments, at least two stabilization devices secure target areas of tissue during use. Stabilization devices can be positioned such that ends of first legs are positioned proximate to each other during use.

Multiple stabilization devices can be positioned such that cross-members are positioned proximate to each other and ends of the legs are positioned such that the openings of a first legs are proximate to each other and the second openings of the second legs are proximate to each other during use. This can allow alignment elements to pass through openings proximate each other in the legs.

Figure 12:
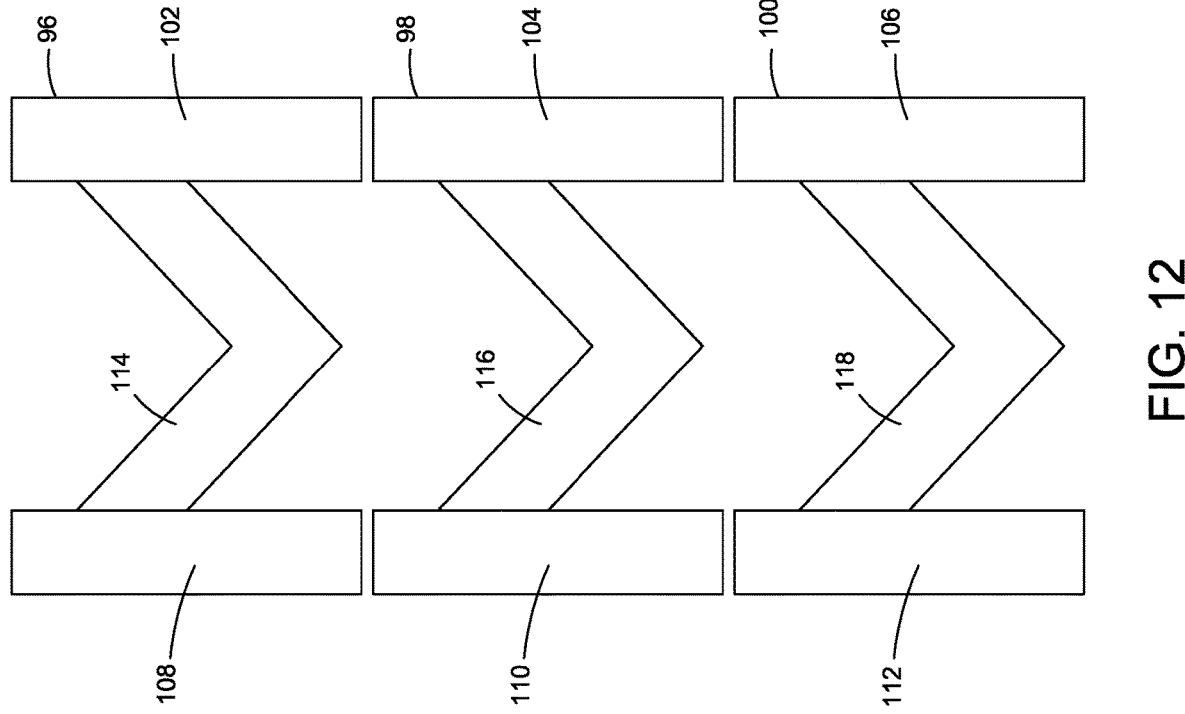
FIG. 12 depicts three stabilization devices positioned in manner to be used together to secure a target area of tissue.

As shown in FIG. 12, three stabilization devices 96, 98, 100 are positioned such that legs 102, 104, 106 and legs 108, 110, 112 align. Thus, the openings in the legs align such that alignment elements can be positioned through the openings such that the alignment elements are positioned in all three stabilization devices. As shown in FIG. 12, the cross-members 114, 116, 118 are aligned such that the cross-members are in the same position relative to each other along a length of the devices. However, in some embodiments stabilization devices can be rotated relative to each other such that the orientations of the stabilization devices from each other.

Figure 13:
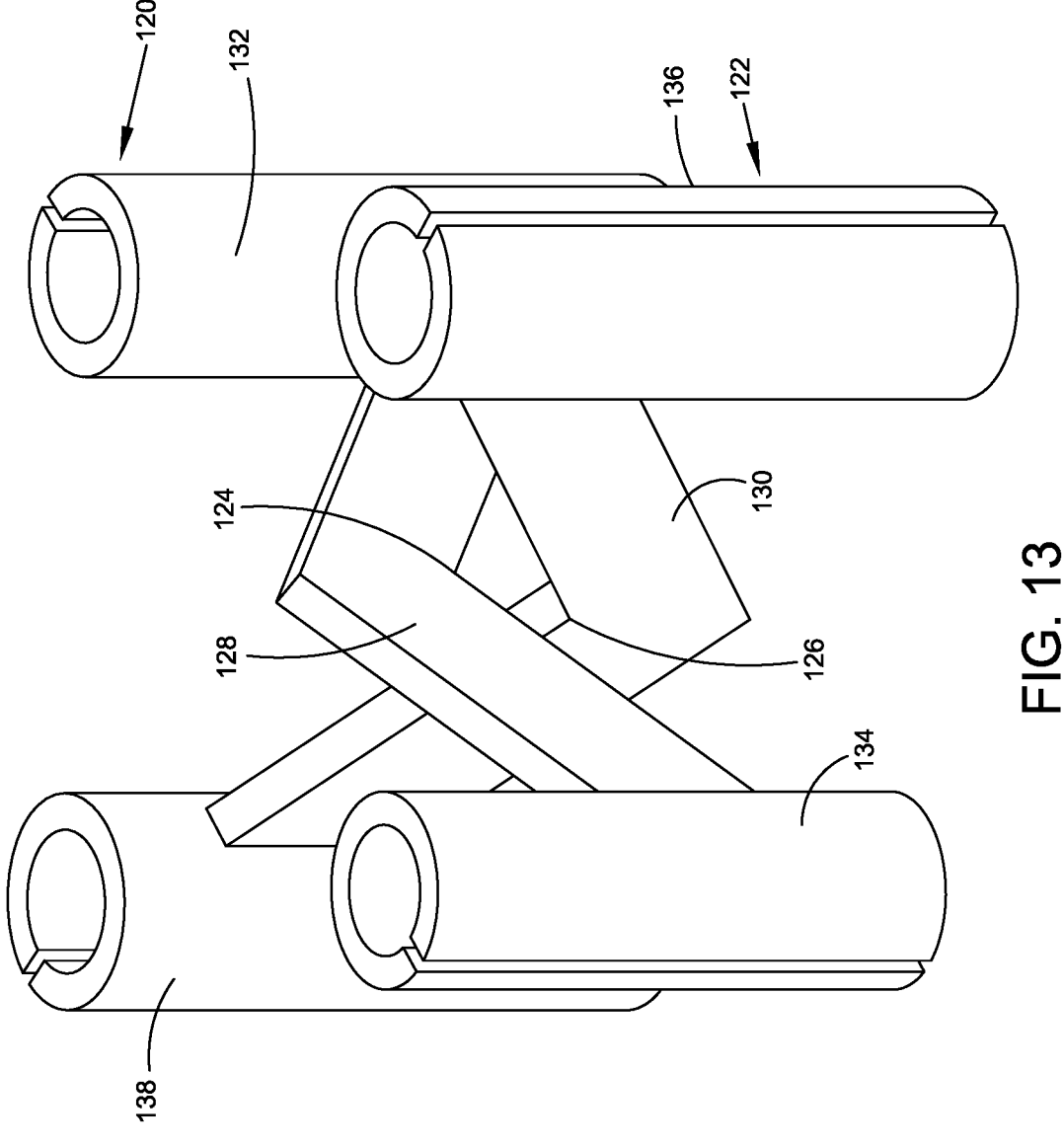
FIG. 13 depicts two stabilization devices positioned in manner to be used together to secure a target area of tissue.

As shown in FIG. 13, stabilization device 120 and stabilization device 122 are offset from each other. Further, stabilization device 120 is positioned upside down relative to stabilization device 122. Center points 124, 126 of cross-members 128, 130 are positioned proximate to each other while legs 132, 134 of stabilization device 120 are offset from legs 136, 138 of stabilization device 122. Offsets can be selected based on requirements of use, anatomy of patient, geometries of the target areas, tissue type, location and/or type of injury, desired distance between the target tissue areas, desired compression, and/or needs of the surgical team.

Methods for implanting a stabilization device can include drilling pilot holes. In some embodiments, pilot holes can be drilled using a drill guide. Pilot holes can be drilled at selected locations in target tissues. Locations for the pilot holes can be selected based on type of procedure, type of injury, anatomy of the patient, needs of the surgical team, etc. Positioning an alignment element in the hole. For example, an alignment pin can be positioned in pilot holes. After positioning of the alignment elements, a cut guide can be positioned over the alignment elements. The cut guide can be used to make a cut for a cross-member of a stabilization device. A stabilization device can then be implanted. In some instances, portions of the stabilization device can engage with the alignment elements.

In some embodiments, the stabilization device can include additional cross-members and/or legs as necessary. Additional cross-members and/or legs can provide additional compression force or distraction force. For example, placement of alignment elements of can affect compression forces applied by the stabilization device during use. In some embodiments, multi-planar compression can be desired. Legs and/or cross-members of the stabilization devices can provide compressive load in multiple directions.

In some instances, stabilization devices can be formed such that the device can apply a selected compression load to target areas. For example, a stabilization device can be positioned such that it provides a selected compression load to bones of an osteotomy or fracture. In particular, a stabilization device can provide fusion site compression via legs while providing bicortical locked or non-locked fixation on perimeter of the device.

Stabilization devices can be used to apply distraction to target areas of tissue. Some of the surfaces of the stabilization device may include coatings and/or surfaces that are compatible with in vivo use and/or that promote bone growth. In some embodiments, portions of a stabilization device can have porous or perforated structures to promote bone growth. Stabilization devices or portions thereof can be coated or wrapped or surfaced treated to provide bony in-growth or through-growth. In some embodiments, stabilization devices or elements thereof can be formed from a material that possesses a structure conducive to bony in-growth or through-growth, such as a porous mesh, hydroxyapatite, or other porous surface. Stabilization devices can be covered with various other coatings such as antimicrobial, antithrombotic, and osteoinductive agents, and/or a combination thereof.

Stabilization devices can include sections having varying wall thicknesses. For example, as shown in FIG. 7 a wall thickness 70 of leg 66 and a wall thickness 74 of cross-member 72 differs. Wall thicknesses of legs can be in range from about XX to XX mm and wall thicknesses of cross-members can be in range from about XX to about XX mm. A length 76 of cross-member 72 as shown in FIG. 7 is constant along a width of the cross-member 72. In alternate embodiments, a length of a cross-member may vary along a width of the cross-member.

The instrumentation for implanting stabilization devices can include a drill, a cutting element such as a drill bit, burr, etc., a drill peck, a broach, a cutting guide, a tap, and/or an insert device can be useful for preparing the target area of tissue and implanting the stabilization devices.

Stabilization devices described herein may be used in conjunction with other orthopedic devices such as screws, plates, etc. to fix and/or fuse target areas of bone.

Positioning of stabilization devices into a target area of bone may include placing alignment elements such as guide wires into a bone piece. Alignment elements can be used to position a cutting guide. The cutting guide can be used to cut an opening in tissue for a stabilization device.

In some embodiments, stabilization devices can be combined with a plate suitable for attachment to bone or the like via screws. For example, a stabilization device can compress target areas of bone or tissue. For example, a plate structure and a stabilization device can be arranged in a side-by-side arrangement. A plate and fasteners used to secure the plate can be parallel to, perpendicular to, or positioned at another angle relative to a leg of the stabilization device.

Stabilization devices can provide compression by positioning and/or structure of alignment elements, legs, and/or cross-members. Legs can have various alignments and configurations. Stabilization devices can be used to oppose bone surfaces, whether in fusion or fracture care.

Stabilization devices can be implanted using a cutting guide. Cutting guides can be structured to allow for cutting of tissue positioned between alignment elements. For example, cutting guides can have openings that couple to alignment elements positioned in target areas of bone.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A stabilization device comprising:
   a first cannulated leg defining a circular cross section and including a first longitudinal slot extending along an outer wall of the leg;
   a second cannulated leg substantially parallel to the first leg and defining a circular cross section and including a second longitudinal slot extending along an outer wall of the leg; and
   a cross-member coupling the first leg to the second leg; wherein the cross-member couples to the first and second legs at a predetermined distance from both ends of each of the first and second legs.

2. The stabilization device of claim 1 wherein each of the first and second legs comprise an opening along longitudinal axes of the first and second legs.

3. The stabilization device of claim 2 wherein each of the openings is structured to engage an alignment element.

4. The stabilization device of claim 2 wherein each of the openings is structured to engage a pin.

5. The stabilization device of claim 1 wherein the first and second legs and the cross-member are formed from a metal alloy.

6. The stabilization device of claim 1 wherein the first and second legs and the cross-member are formed from Nitinol.

7. A stabilization device comprising:

a first cannulated leg defining a first longitudinal slot arranged in a wall of the leg;

a second cannulated leg substantially parallel to the first leg and defining a second longitudinal slot arranged in a wall of the leg; and a V-shaped cross-member including two linear segments that meet at a vertex and coupling the first leg to the second leg;

wherein at least one end of each of the first and second legs extend beyond an outermost edge of the cross-member along a longitudinal axis of the stabilization device.

8. The stabilization device of claim 7 wherein the at least one end of each of the first and second legs extends beyond an outermost edge of the cross-member such that a plane that includes a first end of the first leg and a first end of the second leg does not contact any portion of the cross-member.

9. The stabilization device of claim 7 wherein the first and second legs and the cross-member are formed from a metal alloy.

10. The stabilization device of claim 7 wherein the first and second legs and the cross-member are formed from Nitinol.

11. The stabilization device of claim 7 wherein each of the first and second legs comprise an opening along longitudinal axes of the first and second legs.

12. The stabilization device of claim 11 wherein each of the openings is structured to engage an alignment element.

13. The stabilization device of claim 11 wherein each of the openings is structured to engage a pin.

14. A stabilization device system comprising:

a first alignment element;

a second alignment element;

a cut guide;

a stabilization device comprising:

a first leg having a first opening positioned along a first longitudinal axis of the first leg;

a second leg having a second opening positioned along a second longitudinal axis of the second leg; and a V-shaped cross-member including two linear segments that meet at a vertex and coupling the first leg to the second leg; wherein at least one end of each of the first and second legs extend beyond an outermost edge of the cross-member along a longitudinal axis of the stabilization device; and an inserter device.

15. The stabilization device of claim 14 wherein the first opening engages the first alignment element.

16. The stabilization device of claim 14 wherein the second opening engages the second alignment element.

17. An orthopedic stabilization device comprising:

a first cannulated leg defining a first longitudinal slot arranged in a wall of the leg and having a first opening;

a second cannulated leg defining a second longitudinal slot arranged in a wall of the leg and having a second opening; and a V-shaped cross-member including two linear segments that meet at a vertex and coupling the first leg to the second leg;

wherein the orthopedic stabilization device is configured to secure a target area of tissue during use.

18. An orthopedic implant system comprising:

at least two stabilization devices comprising:

a first cannulated leg defining a first longitudinal slot arranged in a wall of the leg and having a first opening;

a second cannulated leg defining a second longitudinal slot arranged in a wall of the leg and having a second opening; and a V-shaped cross-member including two linear segments that meet at a vertex and coupling the first leg to the second leg; and at least two alignment elements for coupling to openings of legs;

wherein a first of the at least two alignment elements couples the first legs of the at least two stabilization devices and a second of the at least two alignments couples the second legs of the at least two stabilization devices.

* * * * *